(12) United States Patent
Zhang et al.

(10) Patent No.: US 8,110,667 B2
(45) Date of Patent: Feb. 7, 2012

(54) METHOD FOR CONVERSION OF CARBOHYDRATE POLYMERS TO VALUE-ADDED CHEMICAL PRODUCTS

(75) Inventors: Zongchao C. Zhang, Norwood, NJ (US); Heather M. Brown, Kennewick, WA (US); Yu Su, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 689 days.

(21) Appl. No.: 12/110,997

(22) Filed: Apr. 28, 2008

(65) Prior Publication Data

US 2009/0270608 A1 Oct. 29, 2009

(51) Int. Cl.
*C07H 15/00* (2006.01)
*C07H 17/00* (2006.01)
*C07G 3/00* (2006.01)

(52) U.S. Cl. .................... 536/18.6; 536/18.5; 536/124

(58) Field of Classification Search .................... None
See application file for complete search history.

(56) References Cited

U.S. PATENT DOCUMENTS

| 4,113,762 | A  | 9/1978 | Gaenzler et al. |
| 6,518,440 | B2 | 2/2003 | Lightner |
| 2005/0038302 | A1 | 2/2005 | Hedrick et al. |

FOREIGN PATENT DOCUMENTS

| EP | 0498305 A1 | 12/1992 |
| EP | 1559750 A2 | 3/2005 |
| WO | 2006063220 A2 | 6/2006 |
| WO | 2008003643 A1 | 1/2008 |
| WO | 2008019219 A1 | 2/2008 |
| WO | 2008100577 A1 | 8/2008 |
| WO | 2009071181 A2 | 6/2009 |

OTHER PUBLICATIONS

Yang et al. Applied Catalysis A (2003), vol. 241, pp. 363-373.*
Werpy, T. et al., Top Value Added Chemicals from Biomass vol. I—Results of Screening for Potential Candidates from Sugars and Synthesis Gas, DOE/GO-102004-1992 (Produced for the U.S. Department of Energy (DOE) by the National Renewable Energy Laboratory, a DOE Laboratory, Aug. 2004.
Dieter, et al, Ionic Structure and Interactions in 1-Methyl-3 ethylimidazolium Chloride-A1C13 Molten Salts, J. Am. Chem Soc. 1988, 110, pp. 2722-2726.
Lansalot-Matras, et al., Dehydration of fructose into 5-hydroxymethylfurfural in the presence of ionic liquids, Catalysis Communications, vol. 4, (2003), pp. 517-520.
Moreau, et al., Dehydration of fructose and sucrose into 5-hydroxymethylfurfural in the presence of 1-H-3-methyl imidazolium chloride acting both as solvent and catalyst, Journal of Molecular Catalysis A: Chemical 253 (2006) pp. 165-169.
Fischer, S. et. al., Inorganic molten salts as solvents for cellulose, Cellulose, vol. 10, Jan. 1, 2003, 227-236.
Fischer, S., Unconventional Dissolution and Derivatization of Cellulose, Lenzinger Berichte, vol. 83, 2004, 71-78.
Heinze, Thomas et al., Ionic Liquids as Reaction Medium in Cellulose Functionalization, Macromolecular Bioscience, vol. 5, Jan. 1, 2005, 520-525.
Rinaldi, Roberto, et al, Depolymerization of Cellulose Using Solid Catalysts in Ionic Liquids, Angewandte Chemie, International Edition, vol. 47, No. 42, Sep. 22, 2008, 8047-8050.
Su, Yu et al., Single-step conversion of cellulose to 5-hydroxymethylfurlural (HMF), a versatile platform chemical, Applied Catalysis A: General, vol. 361, No. 1-2, Apr. 9, 2009, 117-122.
Binder, Joseph B. et al., Simple Chemical Transformation of Lignocellulosic Biomass into Furans for Fuels and Chemicals, Journal of the American Chemical Society, Jan. 21, 2009, 1979-1985.
Buo, P. J. et al., One-step hydrogenolysis of dimethyl maleate to tetrahydrofuran over chromium-modified Cu-B/gamma-A1203 catalysts, Journal of Molecular Catalysis, A, Chemical, vol. 256, No. 1-2, Aug. 18, 2006, 164-170.
Garcia, K. E. et al., Characterization of akageneite synthesized in presence of Al<3+>, and Cu<2+> ions and urea, Materials Chemistry and Physics, vol. 112, No. 1, May 15, 2008, 120-126.

* cited by examiner

*Primary Examiner* — Patrick Lewis
(74) *Attorney, Agent, or Firm* — James D. Matheson

(57) ABSTRACT

Methods are described for conversion of carbohydrate polymers in ionic liquids, including cellulose, that yield value-added chemicals including, e.g., glucose and 5-hydroxylmethylfurfural (HMF) at temperatures below 120° C. Catalyst compositions that include various mixed metal halides are described that are selective for specified products with yields, e.g., of up to about 56% in a single step process.

25 Claims, 3 Drawing Sheets

METHOD FOR CONVERSION OF CARBOHYDRATE POLYMERS TO VALUE-ADDED CHEMICAL PRODUCTS

This invention was made with Government support under Contract DE-AC05-76RLO1830 awarded by the U.S. Department of Energy. The Government has certain rights in the invention.

FIELD OF THE INVENTION

The invention generally relates to conversion of carbohydrates, and more particularly, to conversion of carbohydrate polymers in ionic liquids using mixed metal halide catalysts to obtain value-added chemical products.

BACKGROUND OF THE INVENTION

Cellulose is a complex polymer chain present in biomass. To convert cellulose to other fuels, hydrolysis is necessary to obtain the monomer building blocks from which desired chemicals may be derived. The hydrolysis reaction is strongly affected by structural and compositional features such as crystallinity and polymer chain length, all of which affect the desired product yields. At present, depolymerization is a recognized bottleneck in the conversion of cellulose feeds. While considerable research effort has been aimed at improving cellulose depolymerization processes in aqueous systems, progress has been limited, in part, due to the lack of solubility of cellulose in water. Enzymatic hydrolysis of cellulose is effective but is characteristically slow at ambient temperatures, and is also sensitive to contaminants originating from the various biomass components. Mineral acids have been extensively investigated to catalyze hydrolysis at a variety of acid concentrations and temperatures, but degradation of resulting products continues to be an issue. One such product, 5-hydroxymethylfurfural (HMF), also known as 5-Hydroxymethyl-2-furaldehyde, is a versatile platform chemical for the production of a broad range of chemicals and fuels currently produced from petroleum. It is therefore desirable to be able to use cellulose feeds directly as a source of glucose for production of HMF. Inability to hydrolyze cellulose to glucose at low temperature presents a substantial barrier to direct utilization of cellulose. Accordingly, new methods are needed for converting carbohydrate polymers at low temperatures to value-added chemicals. Advantages and novel features of the present invention will be set forth hereafter, and will be readily apparent from the descriptions and demonstrations herein. These descriptions should be seen as illustrative of the invention and not as limiting in any way.

SUMMARY OF THE INVENTION

The present invention is a process for selective conversion of carbohydrate polymers to value-added intermediate and end-use chemicals. The process includes: heating a carbohydrate polymer at a preselected temperature in an ionic liquid that includes a catalyst comprising a preselected ratio of at least two metal halides or metal salts for a time sufficient to convert the carbohydrate polymer to desired carbohydrate derivatives and products. Carbohydrate polymers include, but are not limited to, e.g., cellulose, hemicellulose, cellobiose, maltodextrin, starch, or other selected carbohydrates. Reaction processes described herein employ ionic liquids as a reaction medium and various mixed metal halides as reaction catalysts. In the reaction medium, these mixed metal halides catalyze the necessary decrystallization and hydrolysis reactions for conversion of the carbohydrate polymers or parent polysaccharides to desired and/or value-added reaction products. In various embodiments, the mixed metal halide catalyst includes $CuCl_2$ and at least one other metal halide, e.g., $CrCl_2$, $CrCl_3$, $PdCl_2$, $FeCl_3$, $LaCl_3$, $NiCl_2$, $CoCl_2$, but is not limited thereto. The mixed metal halide catalyst includes at least two metal halides, or metal salts, with a first metal halide or metal salt comprising from 50 percent to 99 percent of the total moles of catalyst and a second metal halide or metal salt comprising from 50 percent to 1 percent of the total moles of catalyst. In another embodiment, the carbohydrate polymer is cellulose, the catalyst is a paired metal halide, e.g., [$CuCl_2$:$CrCl_2$], and the carbohydrate product includes HMF. In another embodiment, the carbohydrate product includes a carbohydrate monomer, e.g., glucose. In another embodiment, the carbohydrate product includes HMF. Temperatures and reaction times are selected to maximize the selected carbohydrate products and to minimize product degradation. Temperatures for conversion are preferably in the range from about 100° C. to about 180° C. More preferably, temperatures for conversion are below about 120° C. Time to achieve conversion of carbohydrate polymers is preferably a time in the range from about 0.01 hours to about 8 hours, but is not limited. A more complete appreciation of the invention will be readily obtained by reference to the following description of the accompanying drawings in which like numerals in different figures represent the same structures or elements.

DETAILED DESCRIPTION OF THE INVENTION

Figure 1:
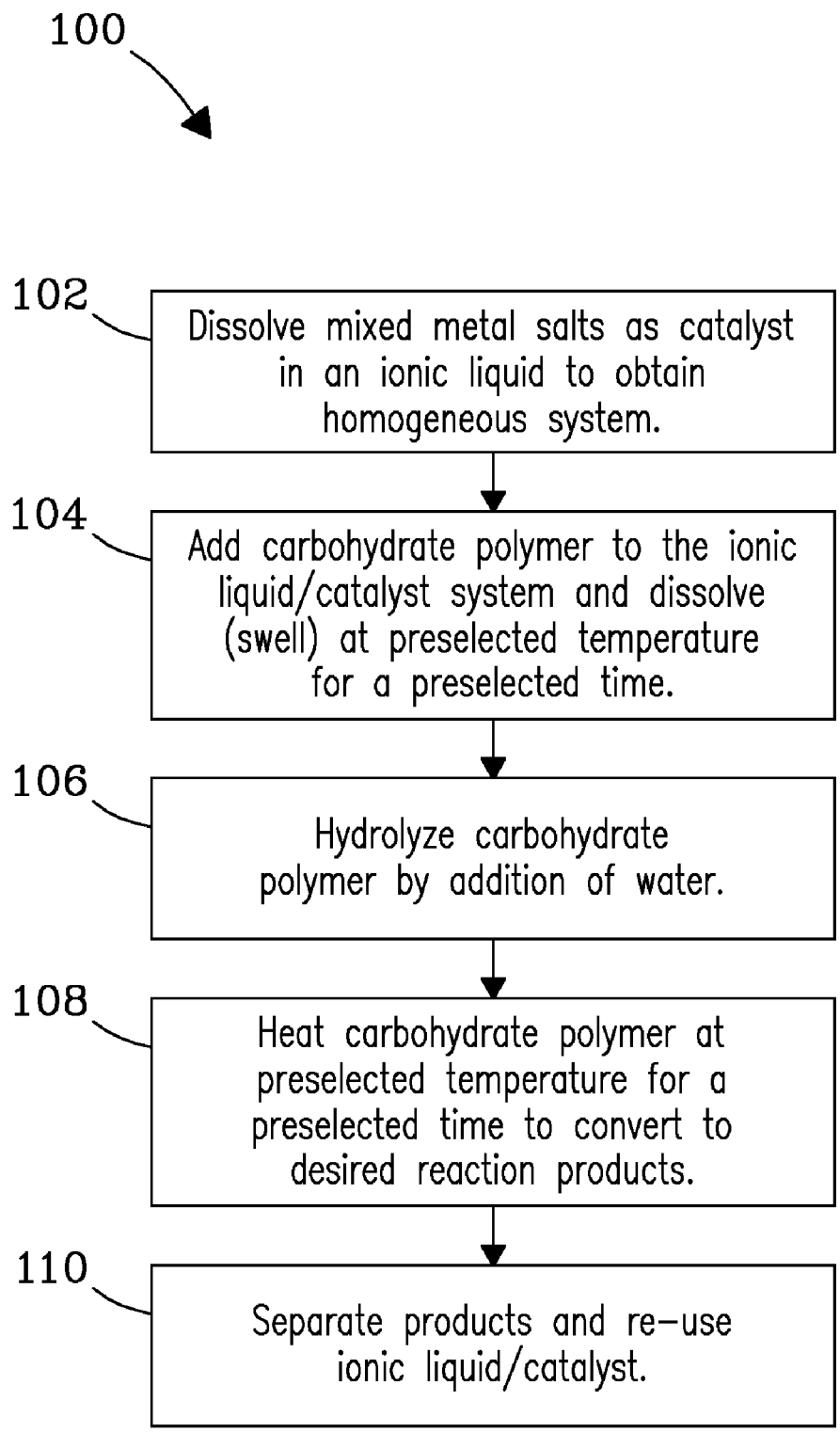
FIG. 1 is a flow chart showing generalized process steps for conversion of carbohydrate polymers in ionic liquids to value-added chemical products.

Described here is a process and catalyst composition for conversion of cellulose and other carbohydrate polymers in an ionic liquid. The following terms are defined for ease of understanding. "Ionic Liquids" are salts that have a melting point, or that are liquid at, temperatures below about 100° C. Ionic liquids used in conjunction with the present invention comprise a 1-$R_1$-3-$R_2$-imidazolium halide, where $R_1$ and $R_2$ are alkyl groups of formula ($C_xH_{2x+1}$) where X=1 to 18. Exemplary ionic liquids include, but are not limited to, e.g., 1-ethyl-3-methylimidazolium chloride ([EMIM]Cl); 1-butyl-3-methylimidazolium chloride ([BMIM]Cl), 1-ethyl-3-methylimidazolium bromide ([EMIM]Br), and combinations thereof. Nomenclature used herein to denote ionic liquids identifies the cationic portion of the ionic liquid, e.g., 1-ethyl-3-methyl-imidazolium, by bracket, e.g., [EMIM] or [EMIM]$^+$. The anionic portion of the ionic liquid, e.g., halides (e.g., Cl$^-$ or Br; or Cl$^-$ or Br$^-$) is identified by placement outside the bracket (e.g., [EMIM]Cl or [EMIM]$^+$Cl$^-$). Unless otherwise noted, nomenclature for ionic liquids with or without ionic charges is used interchangeably, e.g., [EMIM]⁺Cl⁻ or [EMIM]Cl. "Imidazolium" refers to the cationic portion of an ion-forming salt from the imidazole class of heterocyclic aromatic compounds with the following general structure [S1]:

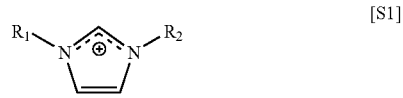
[S1]

Here, $R_1$ and $R_2$ are alkyl groups of formula $(C_xH_{2x+1})$ where X=1 to 18. The following terms are also defined.

Ionic liquids decrystallize a preselected carbohydrate polymer or polysaccharide and provides for the dissolution of the polymer or polysaccharide in the ionic liquid. Dissolution is the chemical process by which the carbohydrate polymer or polysaccharide dissolves into the ionic liquid. As used herein, dissolution encompasses all suitable dissolution temperatures necessary to provide a homogeneous mixture comprising: 1) the carbohydrate polymer, 2) the preselected mixed metal halide (or other selected counter-ion) catalysts, and 3) the ionic liquid, but excludes any depolymerization or hydrolysis of the polymer. "Dissolution temperature", or swell temperature, refers to a preselected temperature that best achieves the desired degree of dissolution of the selected carbohydrate polymer in the selected ionic liquid, which is not limited.

The mixed metal halide (or other metal salt) catalysts described herein for use in conversion of carbohydrate polymers catalyze a chain of necessary conversion reactions in the ionic liquid, including, e.g., hydrolysis and dehydration reactions that yield desired carbohydrate conversion products. The following terms are used herein to describe concentrations of mixed metal halide or mixed metal salt catalysts:

"Total Catalyst Loading" is a quantity defined for the conversion catalyst, given by the equation [1]:

$$[\text{Catalyst Loading (mmol/g)}] = \left( \frac{(mmoles \text{ Catalyst 1}) + (mmoles \text{ Catalyst 2})}{\text{grams Ionic Liquid}} \right) \quad [1]$$

Here, Catalyst 1 is a first metal halide or a first metal salt. Catalyst 2 is a second metal halide or another second metal salt. "Percent catalyst composition" (percent composition) as used herein refers to the percentage that each metal halide or metal salt comprises in the catalyst system that, when added together, equals 100 percent. For a catalyst system comprising $CuCl_2$ and $CrCl_2$ with a percent catalyst composition of [95:5], quantity (mmoles/g ionic liquid) of each metal halide component is given by Equations [2] and [3]:

$$[mmoles \text{ CuCl}_2/\text{g Ionic Liquid}] = \left( \frac{(\text{Total Catalyst Loading}) \times (95)}{100} \right) \quad [2]$$

$$[mmoles \text{ CrCl}_2/\text{g Ionic Liquid}] = \left( \frac{(\text{Total Catalyst Loading}) \times (5)}{100} \right) \quad [3]$$

Hydrolysis is the chemical process by which a carbohydrate polymer or polysaccharide depolymerizes in the presence of, or reacts with, water that leads ultimately to desired conversion products. For example, hydrolysis of cellulose in ionic liquids yields simple sugars and HMF with unexpectedly low yields of contaminants such as levulinic acid. Conversion of carbohydrate polymers in the ionic liquid/mixed metal halide catalyst systems describe herein does not require use of additional acids to effect dehydration. Further, conversion of cellulose and other complex carbohydrates in ionic liquids, catalyzed by mixed metal halide (or other counter-ion) catalysts, exhibits high selectivity to desired chemical products. For example, carbohydrate polymers can be selectively converted to value-added products depending on the choice of selected catalyst, which products include, but are not limited to, e.g., glucose, mannose, and/or HMF. Thus, by appropriate selection of mixed metal halide catalyst, product and yield can be selectively tuned. The term "activity" as used herein is a relative measure of the effectiveness of a selected catalyst to achieve hydrolysis and conversion of a selected carbohydrate polymer to preselected end products. As an example, a 50% conversion achieved by one mixed metal halide catalyst is more active than a catalyst that achieves a 30% conversion. Low catalyst activity is defined herein as a product yield below about 10%. The following terms are defined that have reference to conversion of carbohydrate polymers, described further herein. The term "Selectivity" as used herein is defined by Equation [4]:

$$\text{Selectivity} = \left( \frac{\text{Moles Product Formed}}{\text{Moles Starting Material Reacted}} \right) \quad [4]$$

The term "Conversion" is defined by Equation [5]:

$$\text{Conversion} = 1 - \left( \frac{\text{Moles Unreacted Starting Material}}{\text{Moles Starting Material}} \right) \quad [5]$$

The term "Yield" as used herein is defined by Equation [6]:

$$\text{Yield} = \left( \frac{\text{Moles Product Formed}}{\text{Moles Starting Material}} \right) \quad [6]$$

The furan class of compounds is an exemplary class of conversion products. "Furans" are heterocyclic aromatic, or organic, compounds with general structures [S2] and [S3]:

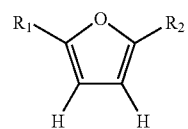
[S2]

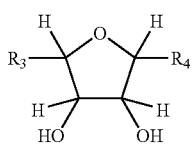
[S3]

Here, $R_1$, $R_2$, $R_3$, and $R_4$ are functional groups including, e.g., H or C; C may further include O and/or H, defining, e.g., aldehyde or alcohol functional groups. "Furan" [CAS Number 110-00-9] $(C_4H_4O)$ is included in this class of compounds having structure [S2], where $R_1$ and $R_2$ are H. 5-hydroxymethylfurfural (HMF) [CAS No. 67-47-0] (chemical formula: $C_6H_6O_3$), also known as "hydroxymethylfurfural", is a chemical derivative of furan, having a structure [S2], where $R_1$ is an alcohol (—$CH_2OH$) group and $R_2$ is an aldehyde (H—C=O) group, described further herein. While conversion of cellulose is described hereafter for purposes of illustrating preferred processes in conjunction with selected catalyst compositions, the disclosure is not intended to be limited to conversion of this exemplary compound, but is intended to be representative of conversion of many varied carbohydrate polymers and polysaccharides. For example, carbohydrate polymers and polysaccharides suitable for conversion by processes of the invention include, but are not limited to, e.g., starch, cellulose, hemicellulose, and cellobiose. No limitations are intended.

Hydrolysis of cellulose to produce glucose, followed by dehydration to produce hydroxymethylfurfural (HMF), requires low temperature conversion reactions because glucose and HMF degrade at high temperature. Paired metal chlorides consisting of, e.g., $CuCl_2$ and an additional metal chloride, e.g., $CrCl_2$, $PdCl_2$, $CrCl_3$, and $FeCl_3$, effectively catalyze cellulose depolymerization in an ionic liquid of 1-ethyl-3-methylimidazolium chloride (i.e., [EMIM]Cl) at temperatures below 120° C. Other imidazolium halides can also be used as ionic liquids. Thus, use of exemplary ionic liquids demonstrated and described herein are not intended to be limitations of ionic liquids suitable for use. Rate of hydrolytic depolymerization of cellulose in the [EMIM]Cl ionic liquid is at least an order of magnitude faster when catalyzed by mixed metal halides of the invention as compared to those catalyzed in the control experiments using a mineral acid. Cellulose conversion catalyzed with a paired [$CuCl_2$:$CrCl_2$] mixed metal halide gave a yield of HMF of about 56%.

FIG. 1 is a process flow chart showing process steps for conversion of carbohydrate polymers, according to an embodiment of the method of the invention. [START]. In one step 102, a catalyst comprising of mixed metal halides or mixed metal salts is prepared by mixing at least two metal halides or mixed metal salts in an ionic liquid and heating the mixture at a preselected temperature to obtain a homogeneous mixture or solution. A preferred mixing temperature for preparation of the catalyst is about 150° C., but is not limited. Total catalyst loading of metal halides or metal salts in the ionic liquid is preferably selected in the range from about 6 mmol/g ionic liquid to about 370 mmol/g ionic liquid; more particularly, in the range from about 12 mmol/g ionic liquid to about 185 mmol/g ionic liquid; and most particularly, in the range from about 18 mmol/g ionic liquid to about 60 mmol/g ionic liquid. Of the total catalyst loading, the two metal halides or metal salts comprise a percent catalyst composition of between about [95:5] percent and about [50:50] percent. More particularly, the percent catalyst composition is between about [99:1] percent to about [70:30] percent. In another step 104, carbohydrate polymer is introduced to the ionic liquid/catalyst system. Polymer is preferably added to the reaction mixture at room temperature for ease of handling. Concentration of carbohydrate polymer introduced to the ionic liquid is in the range from about 10 wt % to about 30 wt %, but can be Lip to the limit of solubility in the selected ionic liquid. Thus, no limitations are intended. In another step 106, carbohydrate polymer is heated in the ionic liquid at a preselected dissolution (swell) temperature and dissolution time sufficient to dissolve (swell) the polymer. Preferred dissolution temperature is between about 100° C. and about 150° C. Preferred dissolution time is between about 30 minutes and 60 minutes, but is not limited thereto. In another step 108, water is added to the reaction mixture to initiate hydrolysis of the polymer. Preferred concentration of water in the ionic liquid is between about 2 wt % and about 20 wt %, but is not limited thereto. Mixture is subsequently heated to a preselected reaction temperature. Preferred reaction temperature is between about 80° C. and about 120° C., but is not limited thereto. In yet another step 110, the carbohydrate polymer is heated in the ionic liquid containing water in the presence of catalyst for a time sufficient to convert the carbohydrate polymer to preselected end products. Reaction temperature for conversion is preferably selected in the range from about at 80° C. to about at 120° C., but is not limited. Time of reaction is typically selected in the range from about 0.01 hours to about 8 hours, but is not limited. In a final step 112, reaction products are separated and recovered from the ionic liquid using separation methods as will be known to those of skill in the chemical arts including, e.g., vacuum distillation, organic solvent extraction, and/or other separation methods that separate organics from hydrophilic solvents [END]. Those of skill in the chemical arts will appreciate that temperatures and reaction times will depend in part on the desired reaction products. Thus, no limitations in scope should be interpreted by the listed reaction temperatures and reaction times. All reaction parameters as will be contemplated or used by those of skill in the art in view of the disclosure are within the scope of the invention.

Figure 2:
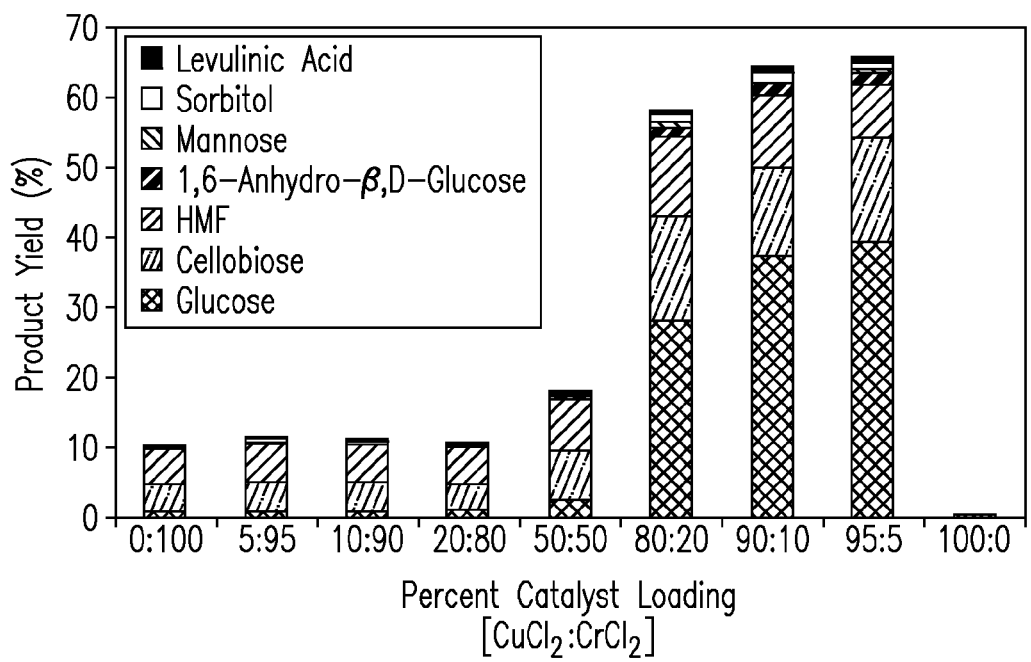
FIG. 2 presents product yields obtained from conversion of cellulose using a paired [$CuCl_2$:$CrCl_2$] metal halide catalyst comprising various quantities of constituent metal halides.

FIG. 2 is a plot showing yields of product chemicals resulting from conversion of cellulose-containing biomass in [EMIM]Cl ionic liquid. Here, a paired [$CuCl_2$:$CrCl_2$] metal halide catalyst comprising various percent compositions of constituent metal halides was used. Cellulose was dissolved for a period of 1 hour at a dissolution (swell) temperature of 100° C. in the [EMIM]Cl ionic liquid prior to conversion. Cellulose feed used for the conversion reaction was about 10 wt % in the ionic liquid (e.g., 50 mg cellulose to 500 mg ionic liquid). Total catalyst loading (combined quantity of $CuCl_2$ and $CrCl_2$) in the paired metal halide catalyst was 37 mmol/g ionic liquid. Reaction (conversion) temperature was 120° C. Time of reaction was 1 hour.

Figure 3:
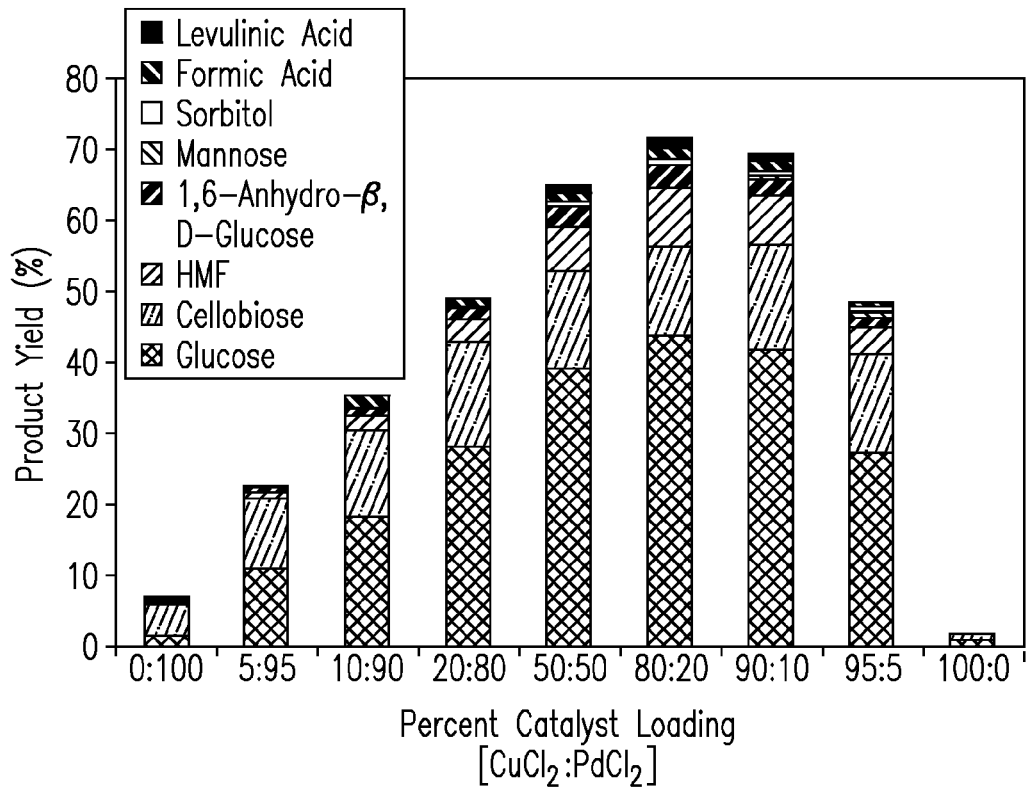
FIG. 3 presents product yields obtained from conversion of cellulose using a paired [$CuCl_2$:$PdCl_2$] metal halide catalyst comprising various quantities of constituent metal halides.

FIG. 3 is a plot showing yields of chemical products from conversion of cellulose in [EMIM]Cl ionic liquid using various percent compositions of [$CuCl_2$:$PdCl_2$] in the paired metal halide catalyst. Total catalyst loading was held constant at 37 mmol/g ionic liquid. Cellulose was allowed to dissolve (swell) in the ionic liquid after addition of the catalyst for 1 hour at 100° C. Reaction period was 0.5 hours at 120° C. In the figure, a total product yield in excess of 70% was obtained, with glucose as a major product, when the catalyst comprised a [80:20] percent composition for the paired [$CuCl_2$:$PdCl_2$] metal halides in the catalyst. Results further indicate that adding as little as 5% $PdCl_2$ in the paired [$CuCl_2$:$PdCl_2$] metal halide catalyst system (i.e., a percent catalyst composition of [95:5]) provides acceptable product yields in the [EMIM]Cl ionic liquid. In the [$CuCl_2$:$PdCl_2$] paired metal halide catalyst system with $CuCl_2$ as the lower concentration component [i.e., a percent catalyst composition of [10:90]), activation effect on the primary $PdCl_2$ metal halide component produces a similar level of activity as when $PdCl_2$ is the lower concentration component (percent catalyst composition of [95:5]), although a greater loading of $CuCl_2$ (i.e., 10%) is necessary to produce a level of activity similar to that obtained with $PdCl_2$ as the lower concentration component (i.e., 5%).

Figure 4:
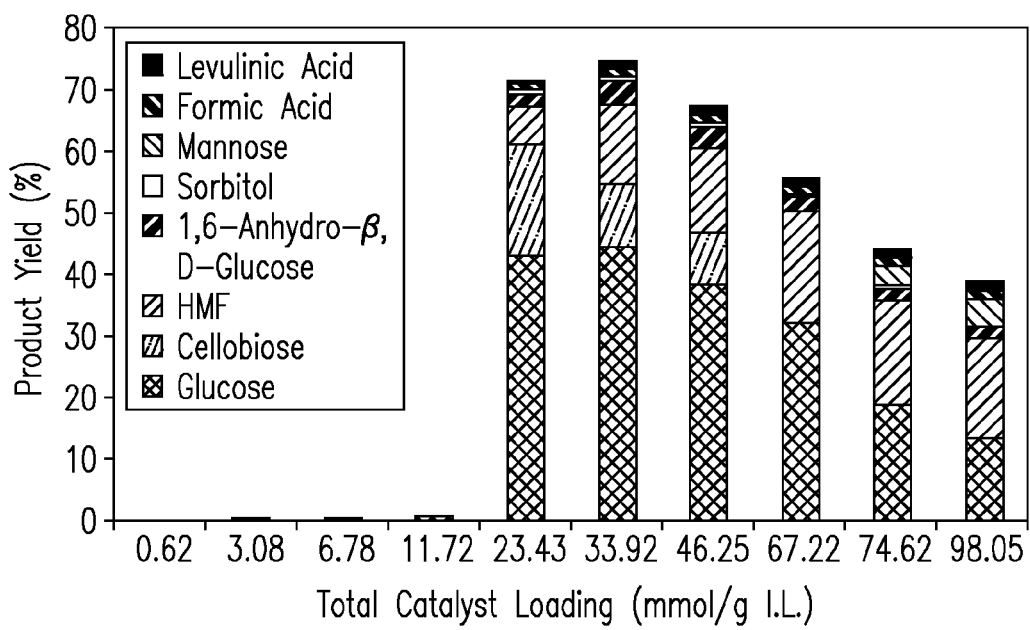
FIG. 4 presents product yields obtained from conversion of cellulose using a paired [$CuCl_2$:$CrCl_2$] metal halide catalyst at selected catalyst loading values.

FIG. 4 is a plot showing product yields from conversion (hydrolysis) of cellulose in [EMIM]Cl ionic liquid using a [$CUCl_2$:$PdCl_2$] mixed metal halide catalyst with a fixed percent catalyst composition of [90:10]. Total metal halide loading in the catalyst was varied. Cellulose was dissolved in [EMIM]Cl at a dissolution (swell) temperature of 100° C. for 1 hour. Reaction period with the catalyst was 1 hour at a temperature of 120° C. In the figure, effect of total metal chloride loading on activity of the [CuCl$_2$:PdCl$_2$] catalyst for conversion of cellulose in [EMIM]Cl ionic liquid is demonstrated. Below a total catalyst loading of ~12 mmol/g ionic liquid (IL), total product yield is only about 2%. Product yield jumps to over 70% when total metal chloride loading is above about 23 mmol/g ionic liquid. Greatest product yield is observed at a total metal chloride loading of about 34 mmol/g ionic liquid. Further increases in catalyst loading decrease yield, presumably a consequence of product degradation, as evidenced by a disappearance of cellobiose product. Similar results were obtained with a [CuCl$_2$:CrCl$_2$] paired metal halide catalyst (fixed [90:10] percent catalyst composition). Here, maximum product yield was reached at a total catalyst loading of about 48 mmol/g ionic liquid in 1 hour at 120° C.

Figure 5:
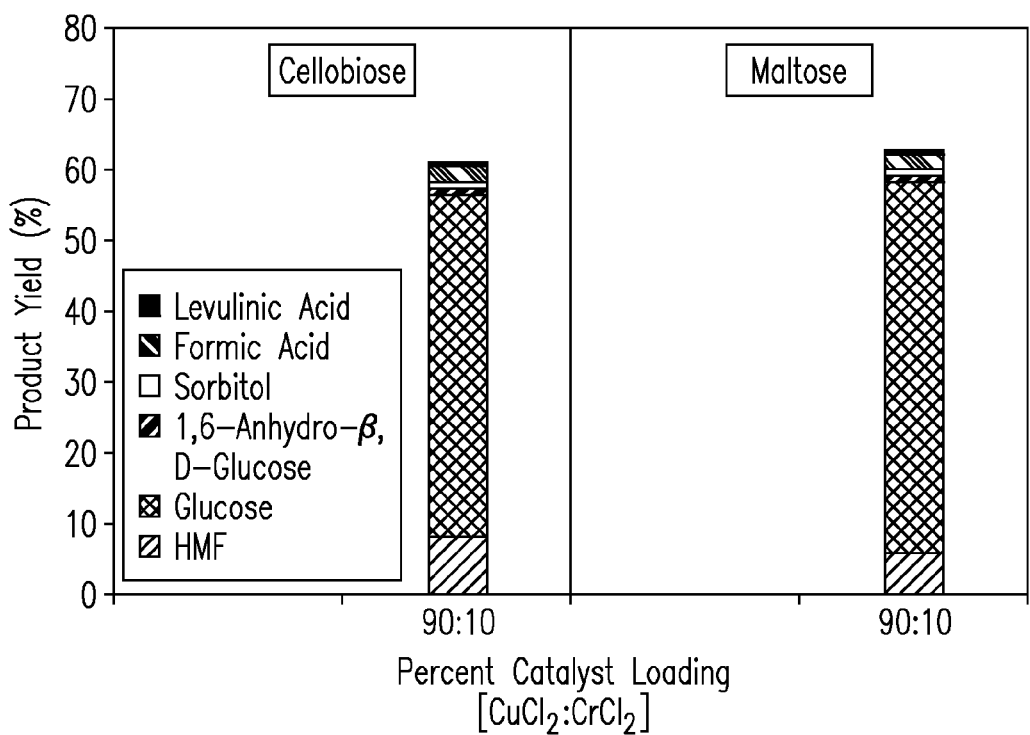
FIG. 5 presents product yields obtained from conversion of cellobiose and maltose using a paired [$CuCl_2$:$CrCl_2$] metal halide catalyst at selected catalyst loading values.

FIG. 5 is a plot showing product yields from hydrolytic conversion of cellobiose and maltose in [EMIM]Cl ionic liquid using a [CUCl$_2$:CrCl$_2$] paired metal halide catalyst with a [90:10] percent catalyst composition. Cellobiose and maltose are simple glucose dimers obtained from hydrolysis of cellulose and starch, respectively. These dimers are linked by: β-1,4-glucosidic bonds (cellobiose) or α-1,4-glucosidic bonds (maltose), respectively. Total catalyst loading was held at about 37 mmol/g ionic liquid. Reaction period was 3 hours at a reaction temperature of 100° C. Addition of a second metal halide, e.g., CrCl$_2$, in the catalyst mixture activates hydrolytic cleavage of α-1,4-glucosidic bonds and β-1,4-glucosidic bonds in the starch and cellobiose polymers, respectively. Here, results show glucose yields from conversion of cellobiose and starch of ~48% and ~53%, respectively. Overall rate for conversion of cellulose and other carbohydrate polymers in an ionic liquid using the mixed metal halide catalysts is a function of rates for individual reaction steps that are activated by the catalyst during the conversion process, including, e.g., decrystallization, depolymerization, and hydrolysis.

The following examples are intended to provide a further understanding of the invention.

EXAMPLE 1

Control: No Catalyst 200 mg (99%) cellulose was mixed in 2 g (99.5%) [EMIM]Cl ionic liquid. 50 µL H$_2$O was added and the mixture was heated at 180° C. No catalyst was added. Maximum yield of glucose was 24%, obtained in 25 minutes. 5% HMF was formed. Product degradation decreased glucose yield at longer reaction times. Glucose yield dropped to 5% after 70 minutes. A comparable reaction mixture heated to 160° C. gave a maximum yield of 32% glucose in 160 minutes; about 7% HMF was formed. Longer reaction times decreased glucose yield. Glucose yield dropped to 12% after 250 minutes.

EXAMPLE 2

Conversion of Cellulose

Paired [CUCl$_2$:CrCl$_2$] Metal Halide Catalyst

Conversion of cellulose (C$_{12}$H$_{22}$O$_{11}$), a carbohydrate polymer derivative of cellulose comprising two glucose units, using a mixed metal catalyst was investigated. 500 mg (99.5%) [EMIM]Cl was mixed with a paired [CuCl$_2$:CrCl$_2$] metal halide catalyst and heated at 150° C. for 0.5 hours to obtain a homogeneous mixture. Percent catalyst composition values for CuCl$_2$ and CrCl$_2$ were varied in different experiments, with the total catalyst loading held constant at 37 mmol/g ionic liquid. 50 mg (99.5%) cellulose was added and heated in the ionic liquid at a dissolution (swell) temperature of 100° C. for 1 hour to dissolve the cellulose. 50 µL H$_2$O was added to initiate hydrolysis. Conversion was conducted at a reaction temperature of 120° C. for 1 hour. In another experiment, reaction temperature was 120° C. with a reaction time of 2 hours. Results are shown in TABLE 1 and TABLE 2, respectively.

TABLE 1

| (DTemp, DTime); (RTemp, RTime): (100° C., 1 hour); (120° C., 1 hour) | | | | | | | |
|---|---|---|---|---|---|---|---|
| | [CuCl$_2$:CrCl$_2$] (percent composition): | | | | | | |
| | 5:95 | 10:90 | 17:83 | 50:50 | 83:17 | 90:10 | 95:5 |
| Product yield (%) | 9 | 9 | 9 | 15 | 53 | 61 | 61 |

TABLE 2

| (DTemp, DTime); (RTemp, RTime): (100° C., 1 hour); (120° C., 2 hours) | | | | | | | |
|---|---|---|---|---|---|---|---|
| | [CuCl$_2$:CrCl$_2$] (percent composition): | | | | | | |
| | 5:95 | 10:90 | 17:83 | 50:50 | 83:17 | 90:10 | 95:5 |
| Product yield (%) | 27 | 30 | 34 | 51 | 63 | 63 | 63 |

DTemp = Dissolution (Swell) Temperature;
DTime = Dissolution Time;
RTemp = Reaction Temperature;
RTime = Reaction Time.

Products from conversion of cellulose include, but are not limited to, e.g., glucose; fructose; mannose; formic acid; levulinic acid; 1,6-anhydro-β,D-glucose; and HMF. In TABLE 1, with a 1 hour reaction time, product yields were greatest with the mixed metal halide catalyst at percent catalyst composition values of [83:17], [90:10], and [95:5], respectively. In TABLE 2, with a 2 hour reaction time, product yields were again greatest with the mixed metal halide catalyst at percent catalyst composition values of [83:17], [90:10], and [95:5], respectively. A good yield was also obtained at a percent catalyst composition value of [50:50]. Overall, product yields increased with increasing reaction period.

EXAMPLE 3

Conversion of Cellulose

Paired [Cucl$_2$:Pdcl$_2$] Metal Halide Catalyst

Conversion of cellulose using another mixed metal halide catalyst, i.e., [CuCl$_2$:PdCl$_2$], was investigated. Procedure of Example 2 was repeated. Percent catalyst composition values of CuCl$_2$ and PdCl$_2$ in the metal halide catalyst were varied, with a total loading of metal halides in the catalyst held constant at 37 mmol/g ionic liquid. Cellulose was added and dissolved in the ionic liquid at a dissolution (swell) temperature of 100° C. for 1 hour. Reaction temperature was 120° C. with a reaction time of 0.5 hours. Results are presented in TABLE 3.

TABLE 3

(DTemp, DTime); (RTemp, RTime): (100° C., 1 hour); (120° C., 0.5 hours)

| | [CuCl$_2$:PdCl$_2$] (percent composition): | | | | | | |
|---|---|---|---|---|---|---|---|
| | 5:95 | 10:90 | 17:83 | 50:50 | 83:17 | 90:10 | 95:5 |
| Product yield (%) | 18 | 33 | 43 | 61 | 68 | 65 | 43 |

DTemp = Dissolution (Swell) Temperature;
DTime = Dissolution Time;
RTemp = Reaction Temperature;
RTime = Reaction Time.

Products from conversion of cellulose include, but are not limited to, e.g., glucose; fructose; mannose; formic acid; levulinic acid; 1,6-anydro-β,D-glucose; and HMF. Results show product yield was greatest using a [83:17] percent catalyst loading for metal halides in the mixed metal halide catalyst. Moderate yields were obtained at loadings of [90:10] and [50:50], respectively. Lowest yields were obtained at a percent catalyst loading value of [90:10] and [17:83], respectively.

EXAMPLE 4

Conversion of Cellulose

Paired Metal Halide Catalyst Comprising Cucl$_2$ and Another Metal Halide

Conversion of cellulose was investigated using another mixed metal catalyst comprising [CuCl$_2$] and various secondary metal chlorides. Procedure of Example 2 was repeated. Metal halides in the catalyst were fixed at a [90:10] percent catalyst composition. Total catalyst loading of metal halides in the catalyst was held constant at 37 mmol/g ionic liquid. Cellulose was added and dissolved in the ionic liquid at a dissolution (swell) temperature of 100° C. for 1 hour. Reaction temperature was 100° C. with a reaction time of 4 hours. Results are presented in TABLE 4 and TABLE 5.

TABLE 4

(DTemp, DTime); (RTemp, RTime): (100° C., 1 hour); (100° C., 4 hours)
Percent catalyst composition of CuCl$_2$ to 2$^{nd}$ metal chloride: [90:10]

| | 2$^{nd}$ metal chloride: | | | | | |
|---|---|---|---|---|---|---|
| | CrCl$_3$ | FeCl$_2$ | FeCl$_3$ | PdCl$_2$ | NiCl$_2$ | AlCl$_3$ |
| Total product yield (%) | 57 | 58 | 63 | 59 | 57 | 55 |

TABLE 5

(DTemp, DTime); (RTemp, RTime): (100° C., 1 hour); (100° C., 4 hours)
Percent catalyst composition of CuCl$_2$ to 2$^{nd}$ metal chloride: [90:10]

| | 2$^{nd}$ metal chloride: | | |
|---|---|---|---|
| | LaCl$_3$ | MnCl$_2$ | PtCl$_2$ |
| Product yield (%) | 24 | 29 | 77 |

DTemp = Dissolution (Swell) Temperature;
DTime = Dissolution Time;
RTemp = Reaction Temperature;
RTime = Reaction Time.

Conversion products from cellulose include, but are not limited to, e.g., cellobiose; glucose; fructose; mannose; formic acid; levulinic acid; 1,6-anydro-β,D-glucose; and HMF. Results in TABLE 4 and TABLE 5 show that various secondary metal halides can be added as a component with CuCl$_2$ in a mixed metal halide catalyst that give good product yields for conversion of cellulose. Here, highest activity for conversion of cellulose is observed with PtCl$_2$ as the secondary metal halide component in the mixed metal halide catalyst. Moderate activity is observed with chlorides of Fe, Pd, Cr, Ni, and Al as secondary metal halides in the catalyst. Lowest activity is observed with LaCl$_3$ and MnCl$_2$ as secondary metal halides.

EXAMPLE 5

Conversion of Cellulose

Paired Metal Salt Catalyst with Alternate Counterion

Effect of a different counterion (SO$_4^{2-}$) on the activity of the mixed metal salt [CuSO$_4$:CrCl$_3$] catalyst in conversion of carbohydrate polymers was investigated as a function of dissolution (swell) temperature. Procedure of Example 2 was repeated. A mixed metal catalyst comprising [CUSO$_4$:CrCl$_3$] was used. Percent catalyst composition values of CuSO$_4$ to CrCl$_3$ in the catalyst were varied, while total catalyst loading of metal salts in the catalyst was held constant at 37 mmol/g ionic liquid. Cellulose was dissolved at 120° C. for 1 hour. Reaction temperature was 120° C. with a reaction time of 1 hour. Results are presented in TABLE 6.

TABLE 6

(DTemp, DTime); (RTemp, RTime): (120° C., 1 hour); (120° C., 1 hour)

| | [CuSO$_4$:CrCl$_3$] (percent composition): | | | | | |
|---|---|---|---|---|---|---|
| | 90:10 | 86:14 | 75:25 | 50:50 | 33:67 | 20:80 |
| Total product yield (%): | 50 | 56 | 72 | 72 | 52 | 53 |

DTemp = Dissolution (Swell) Temperature;
DTime = Dissolution Time;
RTemp = Reaction Temperature;
RTime = Reaction Time.

Conversion products from cellulose include, but are not limited to, e.g., cellobiose; glucose; fructose; mannose; formic acid; levulinic acid; 1,6-anydro-β,D-glucose; and HMF. Listed product yields do not total 100%, as some polymeric products remained uncharacterized by HPLC. Results indicate that counterion exhibits little effect on product yields. In TABLE 6, conversion results are directly tied to concentrations of the metals in the mixed metal catalyst, with the secondary metal component having a significant effect on conversion. Results from experiments at various dissolution (swell) temperatures show that, in general, increasing dissolution temperature increases product yields. Results are attributed to better cellulose depolymerization in the ionic liquid at higher temperature, and thus more effective conversion of cellulose.

EXAMPLE 6

Conversion of Cellulose

Paired [CUCl$_2$:CrCl$_3$] Metal Halide Catalyst

Effect of dissolution time and temperature on conversion of carbohydrate polymers was investigated. Procedure of Example 2 was repeated. A mixed metal chloride catalyst of [CUCl$_2$:CrCl$_3$] was used. Percent catalyst composition values for $CuCl_2$ to $CrCl_3$ were varied while total catalyst loading of metal salts in the catalyst was held constant at 37 mmol/g ionic liquid. Cellulose was dissolved at 80° C. for 1 hour. Reaction temperature was 120° C. with a reaction time of 1 hour. Results are presented in TABLE 7.

TABLE 7

(DTemp, DTime); (RTemp, RTime): (80° C., 1 hour); (120° C., 1 hour)

| | [CuCl$_2$:CrCl$_3$] (percent composition): | | | | | |
|---|---|---|---|---|---|---|
| | 90:10 | 86:14 | 75:25 | 50:50 | 33:67 | 20:80 |
| Total product yield (%): | 53 | 53 | 50 | 74 | 68 | 62 |

DTemp = Dissolution (Swell) Temperature;
DTime = Dissolution Time;
RTemp = Reaction Temperature;
RTime = Reaction Time.

Conversion products from cellulose include, but are not limited to, e.g., cellobiose; glucose; fructose; mannose; formic acid; levulinic acid; 1,6-anhydro-β,D-glucose; and HMF. Results show that dissolution (swell) temperature and dissolution time effect product yields and distribution of products. Results further show that [CUCl$_2$:CrCl$_3$] at various percent catalyst compositions is an effective catalyst in the conversion of cellulose.

EXAMPLE 7

Conversion of Cellulose

Various Paired Metal Halide Catalysts

Effect of elevated dissolution temperatures and reaction temperatures on conversion of carbohydrate polymers was investigated. Procedure of Example 2 was repeated. Various paired metal halide catalysts were used at various percent catalyst compositions. Loading of metal halide salts in the catalyst was held constant at 37 mmol/g ionic liquid. Various reaction parameters were employed. Results are presented in TABLE 8.

TABLE 8

| | Run Number: | | | |
|---|---|---|---|---|
| | 1 | 2 | 3 | 4 |
| Mixed Metal Halide Catalyst (percent composition): | CuCl$_2$:CrCl$_2$ (17:83) | CuCl$_2$:CrCl$_3$ (83:17) | CuCl$_2$:CrCl$_3$ (10:90) | CuCl$_2$:PdCl$_2$ (83:17) |
| Feed | Cellulose | Cellulose | Cellulose | Cellulose |
| DTemp: | 100° C. | 100° C. | 140° C. | 100° C. |
| DTime: | 1 hour | 1 hour | 0.5 hours | 1 hour |
| RTemp: | 120° C. | 120° C. | 100° C. | 120° C. |
| RTime: | 8 hours | 1 hour | 0.5 hours | 0.5 hours |
| Product Yield (%) | | | | |
| Cellobiose | — | 14.7 | — | 12.6 |
| Glucose | 0.38 | 40 | 2.0 | 43.6 |
| Mannose | 0.33 | 0.33 | 9.2 | 0.86 |
| Sorbitol | 0.69 | 1.04 | 0.52 | 0.86 |
| 1,6-Anhydro-β,D-Glucose | — | 1.73 | 3.4 | 3.2 |
| Formic Acid | — | 0.03 | 1.0 | 1.7 |

TABLE 8-continued

| | Run Number: | | | |
|---|---|---|---|---|
| | 1 | 2 | 3 | 4 |
| Levulinic Acid | 1.59 | 0.71 | 0.72 | 1.3 |
| HMF | 56 | 7.72 | 41.1 | 8.45 |
| Total Yield | 59 | 66.7 | 58.1 | 71.8 |

DTemp = Dissolution (Swell) Temperature;
DTime = Dissolution Time;
RTemp = Reaction Temperature;
RTime = Reaction Time.

Product yields in TABLE 8 do not total 100% due to presence of uncharacterized polymer residues. Results show that $CrCl_2$ and $CrCl_3$ as components of mixed metal catalysts are selective for HMF production with $CrCl_2$ exhibiting the greater selectivity. For example, hydrolysis of cellulose using a [CUCl$_2$:CrCl$_2$] catalyst with a [17:83] percent catalyst composition occurs within 8 hours at a dissolution (swell) temperature of 100° C. (column 1). Here, 95% selectivity to HMF is observed among recovered products, with a yield for HMF of 56%. Using a [CuCl$_2$:CrCl$_3$] catalyst with a [10:90] percent catalyst composition, hydrolysis of cellulose occurs within 0.5 hours (column 3) at a dissolution (swell) temperature of 140° C., with a yield of HMF of 41%. In contrast, glucose is a predominant product obtained with paired metal halide catalysts including, e.g., [CuCl$_2$:CrCl$_3$] (column 2) and [CuCl$_2$:PdCl$_2$] (column 4), at a percent catalyst composition of [83:17], providing yields of glucose of 40 and 44%, respectively. As demonstrated, product selectivity and yields from a conversion reaction of carbohydrate polymers depend in part on dissolution temperature and time, reaction temperature, time of reaction, choice of catalyst, and mole ratios of the metal halides in the mixed metal catalyst. All parameters as will be selected by those of skill in the art in view of the disclosure are within the scope of the invention. No limitations are intended by discussion of the exemplary tests.

EXAMPLE 8

Conversion of Cellulose

Various Paired Metal Salt Catalysts

Effect of dissolution time and temperature on conversion of carbohydrate polymers was investigated. Procedure of Example 2 was repeated. Various paired metal salt catalysts were used. Percent catalyst composition values varied while total catalyst loading of metal salts in the catalyst was held constant at 37 mmol/g ionic liquid. Cellulose was dissolved at 100° C. and 120° C. for 1 hour; and at 140° C. for 0.5 hours. Reaction temperatures included 120° C. with a reaction time of 1 hour; and 80° C. with a reaction time of 4 hours. Results are presented in TABLES 9-11.

TABLE 9

(DTemp, DTime); (RTemp, RTime): (100° C., 1 hour); (120° C., 1 hour)

| | Mixed metal catalyst (percent composition): | | | | | |
|---|---|---|---|---|---|---|
| | CuCl$_2$/CrCl$_3$ (90:10) | CuCl$_2$/CrCl$_3$ (66:14) | CuSO$_4$/CrCl$_3$ (90:10) | CuSO$_4$/CrCl$_3$ (86:14) | CuBr$_2$/CrCl$_3$ (90:10) | CuBr$_2$/CrCl$_3$ (86:14) |
| Product yield (%) | 63 | 61 | 59 | 58 | 42 | 57 |

TABLE 10

| (DTemp, DTime); (RTemp, RTime): (120° C., 1 hour); (120° C., 1 hour) | | | | | |
|---|---|---|---|---|---|
| Mixed metal catalyst (percent composition): | | | | | |
| $CuCl_2$/ $CrCl_3$ (90:10) | $CuCl_2$/ $CrCl_3$ (86:14) | $CuSO_4$/ $CrCl_3$ (90:10) | $CuSO_4$/ $CrCl_3$ (86:14) | $CuBr_2$/ $CrCl_3$ (90:10) | $CuBr_2$/ $CrCl_3$ (86:14) |
| Product yield (%) | | | | | |
| 55 | 55 | 60 | 51 | 46 | 49 |

TABLE 11

| (DTemp, DTime); (RTemp, RTime): (140° C., 0.5 hours); 80° C., 4 hours) | | | | | | | | |
|---|---|---|---|---|---|---|---|---|
| Catalyst (Percent Composition) | | | | | | | | |
| $CuCl_2$/ $CrCl_3$ (90:10) | $CuCl_2$/ $CrCl_3$ (50:50) | $CuCl_2$/ $CrCl_3$ (90:10) | $CuCl$/ $CrCl_2$ (90:10) | $CuCl$/ $CrCl_2$ (50:50) | $CrCl_2$/ $CuCl_2$ (90:10) | $CuCl_2$/ $PdCl_2$ (90:10) | $CuCl_2$/ $PdCl_2$ (50:50) | $CuCl_2$/ $PdCl_2$ (90:10) |
| Product yield (%) | | | | | | | | |
| 45 | 48 | 57 | 22 | 19 | 8 | 46 | 46 | 82 |

DTemp = Dissolution (Swell) Temperature;
DTime = Dissolution Time;
RTemp = Reaction Temperature;
RTime = Reaction Time.

Conversion products from cellulose include, but are not limited to, e.g., cellobiose; glucose; fructose; mannose; formic acid; levulinic acid; 1,6-anhydro-β,D-glucose; and HMF. Results show that dissolution (swell) temperature has a large effect on product yields and distribution of products. Results further show that paired metal halide catalysts are active in conversion of cellulose at various percent catalyst compositions. When quantity of $CuCl_2$, as the primary metal halide, is low (below about 10%), the paired metal chloride catalyst is not sufficiently active for conversion of cellulose at sufficient yield.

EXAMPLE 9

Conversion of Cellulose

Catalyst with Various Mixed Metal Halides

Effect of time of reaction for conversion of carbohydrate polymers was investigated. Procedure of Example 2 was repeated. Various paired metal halide catalysts were used at various percent catalyst compositions. Total catalyst loading of metal halides in the catalyst was held constant at 37 mmol/g ionic liquid. Cellulose was dissolved at 140° C. for 0.5 hours. Reaction temperature was 80° C., with reaction times of 2 hours, 1 hour, and 0.5 hours, respectively. Results are listed in TABLES 12-14.

TABLE 12

| (DTemp, DTime); (RTemp, RTime): (140° C., 0.5 hour); (80° C., 2 hours) | | | | | | | | |
|---|---|---|---|---|---|---|---|---|
| Catalyst (percent composition): | | | | | | | | |
| $CuCl_2$/ $CrCl_3$ (90:10) | $CuCl_2$/ $CrCl_3$ (50:50) | $CuCl_2$/ $CrCl_3$ (90:10) | $CuCl$/ $CrCl_2$ (90:10) | $CuCl$/ $CrCl_2$ (50:50) | $CuCl_2$/ $CrCl_2$ (90:10) | $CuCl_2$/ $PdCl_2$ (90:10) | $CuCl_2$/ $PdCl_2$ (50:50) | $CuCl_2$/ $PdCl_2$ (90:10) |
| Product yield (%) | | | | | | | | |
| 51 | 54 | 70 | 11 | 11 | 6 | 48 | 54 | 62 |

TABLE 13

(DTemp, DTime); (RTemp, RTime): (140° C., 0.5 hour); (80° C., 1 hour)

| | Catalyst (percent composition): | | | | | | | | |
|---|---|---|---|---|---|---|---|---|---|
| | CuCl$_2$/CrCl$_3$ (90:10) | CuCl$_2$/CrCl$_3$ (50:50) | CuCl$_2$/CrCl$_3$ (90:10) | CuCl/CrCl$_2$ (90:10) | CuCl/CrCl$_2$ (50:50) | CuCl$_2$/CrCl$_2$ (90:10) | CuCl$_2$/PdCl$_2$ (90:10) | CuCl$_2$/PdCl$_2$ (50:50) | CuCl$_2$/PdCl$_2$ (90:10) |
| Product yield (%) | 45 | 50 | 63 | 13 | 19 | 8 | 46 | 48 | 60 |

TABLE 14

(DTemp, DTime); (RTemp, RTime): (140° C., 0.5 hours); (80° C., 0.5 hours)

| | Catalyst (percent composition): | | | | | | | | |
|---|---|---|---|---|---|---|---|---|---|
| | CuCl$_2$/CrCl$_3$ (90:10) | CuCl$_2$/CrCl$_3$ (50:50) | CuCl$_2$/CrCl$_3$ (90:10) | CuCl/CrCl$_2$ (90:10) | CuCl/CrCl$_2$ (50:50) | CuCl$_2$/CrCl$_2$ (90:10) | CuCl$_2$/PdCl$_2$ (90:10) | CuCl$_2$/PdCl$_2$ (50:50) | CuCl$_2$ PdCl$_2$ (90:10) |
| Product yield (%) | 55 | 56 | 62 | 22 | 22 | 28 | 53 | 62 | 66 |

DTemp = Dissolution (Swell) Temperature;
DTime = Dissolution Time;
RTemp = Reaction Temperature;
RTime = Reaction Time.

Again, conversion products from cellulose include, but are not limited to, e.g., cellobiose; glucose; fructose; mannose; formic acid; levulinic acid; 1,6-anhydro-β,D-glucose; and HMF. Results show that percent catalyst compositions in the paired metal halide catalyst affect product yields. At low reaction temperature, product yields did not differ significantly at the different reaction times. For any given mixed metal halide catalyst, specific catalyst compositions exist where the paired metal halide catalyst is highly active. When quantity of CuCl$_2$, as the primary metal halide, is low (below about 10%), the paired metal chloride catalyst is not sufficiently active for conversion of cellulose at sufficient yield.

EXAMPLE 10

Conversion of Cellulose

Paired [CuCl$_2$:CrCl$_3$] and [CuSO$_4$:CrCl$_3$] Metal Salt Catalysts

Effect of elevated dissolution temperatures and reaction temperatures on conversion of carbohydrate polymers was investigated. Procedure of Example 2 was repeated. Two different paired metal salt catalysts, [CuCl$_2$:CrCl$_3$] and [CuSO$_4$:CrCl$_3$] were used. A [90:10] percent catalyst composition of metal salts in the catalyst was used. Loading of metal halide salts in the catalyst was held constant at 37 mmol/g ionic liquid. In a first experiment, cellulose was dissolved at 140° C. for 0.5 hours, followed by a reaction period of 0.5 hours, 1 hour, and 1.5 hours at a reaction temperature of 100° C., respectively. In another experiment, cellulose was dissolved at 120° C. for 0.5 hours, followed by a reaction period of 0.5 hours, 1 hour, and 1.5 hours at a reaction temperature of 120° C., respectively. In another experiment, cellulose was dissolved at 120° C. for 1.0 hour, followed by a reaction period of 0.5 hours, 1 hour, and 1.5 hours at a reaction temperature of 120° C., respectively. Results are presented in TABLES 15 and 16, respectively.

TABLE 15

| Mixed-Metal Catalyst (percent composition): | [CuCl$_2$:CrCl$_3$] (90:10) | | |
|---|---|---|---|
| (DTemp, DTime): | (140° C., 0.5 hour) | | |
| (RTemp): | 100° C. | | |
| (RTime): | 0.5 h | 1 h | 1.5 h |
| Product Yield (%): | 58 | 54 | 61 |
| Mixed-Metal Catalyst (percent composition): | [CuCl$_2$:CrCl$_3$] (90:10) | | |
| (DTemp, DTime): | (120° C., 0.5 hour) | | |
| (RTemp): | 120° C. | | |
| (RTime): | 0.5 h | 1 h | 1.5 h |
| Product Yield (%): | 61 | 61 | 60 |
| Mixed-Metal Catalyst (percent composition): | [CuCl$_2$:CrCl$_3$] (90:10) | | |
| (DTemp, DTime): | (120° C., 1 hour) | | |
| (RTemp): | 120° C. | | |
| (RTime): | 0.5 h | 1 h | 1.5 h |
| Product Yield (%): | 58 | 58 | 57 |

TABLE 16

| Mixed-Metal Catalyst (percent composition): | [CuSO$_4$:CrCl$_3$] (90:10) | | |
|---|---|---|---|
| (DTemp, DTime): | (140° C., 0.5 hour) | | |
| (RTemp): | 100° C. | | |
| (RTime): | 0.5 h | 1 h | 1.5 h |
| Product Yield (%): | 57 | 55 | 51 |
| Mixed-Metal Catalyst (percent composition): | [CuSO$_4$:CrCl$_3$] (90:10) | | |
| (DTemp, DTime): | (120° C., 0.5 hour) | | |
| (RTemp): | 120° C. | | |
| (RTime): | 0.5 h | 1 h | 1.5 h |
| Product Yield (%): | 55 | 61 | 61 |
| Mixed-Metal Catalyst (percent composition): | [CuSO$_4$:CrCl$_3$] (90:10) | | |
| (DTemp, DTime): | (120° C., 1 hour) | | |
| (RTemp): | 120° C. | | |
| (RTime): | 0.5 h | 1 h | 1.5 h |
| Product Yield (%): | 57 | 61 | 58 |

DTemp = Dissolution (Swell) Temperature;
DTime = Dissolution Time;
RTemp = Reaction Temperature;
RTime = Reaction Time.

Conversion products from cellulose include, but are not limited to, e.g., cellobiose; glucose; fructose; mannose; formic acid; levulinic acid; 1,6-anhydro-β,D-glucose; and HMF. Results show that at a given percent catalyst composition for metal salts in the catalyst, product yield depends on process conditions, e.g., dissolution and reaction temperatures as well as reaction time.

While preferred embodiments of the invention have been shown and described herein, many changes and modifications may be made without departing from the invention in its broader aspects. The foregoing abstract is neither intended to define the invention of the application, which is measured by the claims, nor is it intended to be limiting as to the scope of the invention in any way. The appended claims are therefore intended to cover all such changes and modifications as fall within the scope of the invention.

We claim:

1. A method for selective conversion of a carbohydrate polymer, to produce a furan product, comprising the step of:
heating a carbohydrate polymer selected from the group consisting of cellulose, hemicellulose, cellobiose, maltodextrin, starch, and combinations thereof in an ionic liquid comprising a 1-$R_1$-3-$R_2$-imidazolium halide of chemical formula $C_xH_{2x+1}$, where $R_1$ and $R_2$ are alkyl groups, and where X=1 to 18 at a preselected temperature with a dual-metal catalyst at a selected ratio for a time sufficient to convert said carbohydrate polymer to said furan product.

2. The method of claim 1, wherein said ionic liquid is selected from the group consisting of: 1-ethyl-3-methylimidazollum chloride ([EMINA]Cl); 1-butyl-3-methylimidazolium chloride ([BMIM]Cl), 1-ethyl-3-methylimidazolium bromide ([EMIM]Br), and combinations thereof.

3. The method of claim 1, wherein said catalyst comprises $CuCl_2$ and at least one other metal halide.

4. The method of claim 3, wherein said at least one other metal halide is selected from the group consisting of: $CrCl_2$, $CrCl_3$, $PdCl_2$, $FeCl_3$, $LaCl_3$, $NiCl_2$, $CoCl_2$, and combinations thereof.

5. The method of claim 4, wherein the at least two metal halides are present at a ratio from about 97:3 to about 50:50 on a percentage basis.

6. The method of claim 1, further comprising the step of dissolving said carbohydrate polymer in said ionic liquid prior to the step of heating said carbohydrate polymer to decrystalize said carbohydrate polymer.

7. The method of claim 1, wherein the step of heating includes heating the carbohydrate polymer at a concentration of up to about 30 wt % in said ionic liquid.

8. The method of claim 1, wherein the carbohydrate polymer is cellulose, the catalyst comprises a preselected ratio of $CuCl_2$ and $CrCl_2$ metal halides, and the carbohydrate product is 5-hydroxylmethylfurfural.

9. The method of claim 1, wherein said preselected temperature is a temperature selected in the range from about 100° C. to about 180° C. and said preselected time for conversion of said carbohydrate polymer is selected in the range from about 0.01 hours to about 8 hours.

10. A system for conversion of carbohydrate polymers, comprising:
a first metal halide and a second metal halide in preselected ionic liquid.

11. The system of claim 10, wherein said first metal halide and said second metal halide are selected from the group consisting of: $CuCl_2$, $CrCl_2$, $CrCl_3$, $PdCl_2$, $FeCl_3$, $LaCl_3$, $NiCl_2$, $CoCl_2$, and combinations thereof.

12. The system of claim 10, wherein said first metal halide and said second metal halide have a ratio preselected in the range from about 95:5 to about 50:50 on a percentage basis.

13. The system of claim 10, wherein said first metal halide and said second metal halide have a ratio preselected in the range from about 99:1 to about 80:20 on a percentage basis.

14. The system of claim 10, wherein said first metal halide and said second metal halide comprise a total metal halide concentration in said ionic liquid in the range from 6 mmol/g ionic liquid to about 37 mmol/g ionic liquid.

15. The system of claim 10, wherein said first metal halide and said second metal halide comprise a total metal halide concentration in said ionic liquid in the range from about 12 mmol/g ionic liquid to about 185 mmol/g ionic liquid.

16. The system of claim 10, wherein said first metal halide and said second metal halide comprise a total metal halide concentration in said ionic liquid in the range from about 18 mmol/g ionic liquid to about 60 mmol/g ionic liquid.

17. A method for selective conversion of a carbohydrate polymer, comprising the step of:
heating the carbohydrate polymer in an ionic liquid comprising 1-$R_1$-3-$R_2$-imidazolium halide wherein $R_1$ and $R_2$ are alkyl groups of chemical formula $C_xH_{2x+1}$ where X=1 to 18, with a catalyst comprising a preselected ratio of at least two metal halides at a preselected temperature for a time sufficient to hydrolyze same, forming a preselected carbohydrate monomer product that includes glucose.

18. The method of claim 17, wherein the first metal halide and second metal halide have a ratio preselected in the range from about 99:1 to about 50:50 on a percentage basis.

19. The method of claim 17, wherein said first metal halide and said second metal halide comprise a total metal halide concentration in said ionic liquid in the range from 6 mmol/g ionic liquid to about 185 mmol/g ionic liquid.

20. A method for selective conversion of a carbohydrate polymer, comprising the step of:
heating the carbohydrate polymer in an ionic liquid comprised of 1-$R_1$-3-$R_2$-imidazolium halide wherein $R_1$ and $R_2$ are alkyl groups of chemical formula $C_xH_{2x+1}$ where X=1 to 18, with a catalyst comprising a preselected ratio of at least two metal halides at a preselected temperature for a time sufficient to dehydrate same, forming a preselected carbohydrate dehydration product that includes 5-hydroxylmethylfurfural.

21. The method of claim 20, wherein the first metal halide and second metal halide have a ratio preselected in the range from about 99:1 to about 50:50 on a percentage basis.

22. The method of claim 20, wherein said first metal halide and said second metal halide comprise a total metal halide concentration in said ionic liquid in the range from 6 mmol/g ionic liquid to about 185 mmol/g ionic liquid.

23. The method of claim 1, wherein the furan is 5-hydroxylmethylfurfural.

24. The method of claim 1, wherein the furan product further includes a member selected from the group consisting of: cellobiose, sorbitol, formic acid, levulinic acid, 1,6-anhydro-β,D-glucose, and combinations thereof.

25. The method of claim 1, wherein the furan product further includes fructose, glucose, mannose, and combinations thereof.

* * * * *

UNITED STATES PATENT AND TRADEMARK OFFICE
CERTIFICATE OF CORRECTION

| | |
|---|---|
| PATENT NO. | : 8,110,667 B2 |
| APPLICATION NO. | : 12/110997 |
| DATED | : February 7, 2012 |
| INVENTOR(S) | : Zongchao C. Zhang, Heather M. Brown and Yu Su |

It is certified that error appears in the above-identified patent and that said Letters Patent is hereby corrected as shown below:

Col. 5, Line 57: Replace "Lip" with -- up --

Col. 12, Line 19: Replace "[CUCl$_2$:CrCl$_2$]" with -- [CuCl$_2$:CrCl$_2$] --

Col. 13, Table 11: Replace "(DTemp, DTime); (RTemp, RTime): (140°C, 0.5 hours); 80° C, 4 hours)" with -- (DTemp, DTime); (RTemp, RTime): (140° C, 0.5 hours); (80° C, 4 hours) --

Signed and Sealed this
Twenty-fourth Day of April, 2012

David J. Kappos
*Director of the United States Patent and Trademark Office*